(12) United States Patent
Allard et al.

(10) Patent No.: US 6,171,579 B1
(45) Date of Patent: Jan. 9, 2001

(54) SYNERGISTICALLY UV-PHOTOPROTECTING TRIAZINE/SILICONE COMPOSITIONS

(75) Inventors: Delphine Allard, Colombes; Christèle Gombert, Saint Gratien, both of (FR)

(73) Assignee: Societe L'Oreal S.A., Paris (FR)

( * ) Notice: Under 35 U.S.C. 154(b), the term of this patent shall be extended for 0 days.

(21) Appl. No.: 09/258,852

(22) Filed: Feb. 26, 1999

(30) Foreign Application Priority Data

Feb. 27, 1998 (FR) .................................................. 98 02416

(51) Int. Cl.[7] .............................. A61K 7/42; A61K 7/44; A61K 7/00; A61K 31/53
(52) U.S. Cl. .............................. 424/59; 424/60; 424/400; 424/401; 514/241
(58) Field of Search ............................... 424/59, 60, 400, 424/401; 514/241

(56) References Cited

FOREIGN PATENT DOCUMENTS

| | | |
|---|---|---|
| 0742003 | 11/1996 | (EP) . |
| 0815835 | 1/1998 | (EP) . |
| 0824909 | 2/1998 | (EP) . |
| 2747037 | 10/1997 | (FR) . |
| 2286774 | 8/1995 | (GB) . |

*Primary Examiner*—Shelley A. Dodson
(74) *Attorney, Agent, or Firm*—Burns, Doane, Swecker & Mathis, L.L.P.

(57) ABSTRACT

The invention relates to novel cosmetic and/or dermatological compositions, in particular for photoprotecting the skin and/or the hair, characterized in that they comprise, in a cosmetically acceptable support in particular of oil-in-water type, (i) as first screening agent, at least one specific 1,3,5-triazine derivative, and (ii) as second screening agent, a silicon derivative containing a benzotriazole function, the said first and second screening agents being present in the said compositions in an amount which is effective for producing synergistic activity with respect to the sun protection factors imparted.

Application to protecting the skin and the hair against the effects of ultraviolet radiation.

28 Claims, No Drawings

SYNERGISTICALLY UV-PHOTOPROTECTING TRIAZINE/SILICONE COMPOSITIONS

BACKGROUND OF THE INVENTION

1. Technical Field of the Invention

This application claims priority under 35 U.S.C. §§ 119 and/or 365 to Patent Application No. 98-02416 filed in France on Feb. 27, 1998; the entire content of which is hereby incorporated by reference.

The present invention relates to novel cosmetic and/or dermatological compositions which are intended more particularly for photoprotecting the skin and/or the hair against ultraviolet radiation (these compositions being referred to more simply hereinbelow as antisun compositions), as well as to their use in the abovementioned cosmetic application. Even more specifically, the invention relates to antisun compositions comprising, in a cosmetically acceptable support, a combination between a first specific screening agent, i.e. a specific 1,3,5-triazine derivative, with at least a second specific screen agent suitably selected from benzotriazole silicones, this combination giving the said compositions, by means of a synergistic effect, improved sun protection factors.

2. Description of the Prior Art

It is known that light radiation with wavelengths of between 280 nm and 400 nm permit tanning of the human epidermis and that rays with wavelengths of between 280 and 320 nm, which are known as UV-B, cause erythema and skin burns which may be harmful to the development of a natural tan; this UV-B radiation should thus be screened out.

It is also known that UV-A rays, with wavelengths of between 320 and 400 nm, which cause tanning of the skin, are liable to induce an adverse change therein, in particular in the case of sensitive skin or skin which is continually exposed to solar radiation. UV-A rays in particular cause a loss of skin elasticity and the appearance of wrinkles, leading to premature ageing. They promote triggering of the erythemal reaction or amplify this reaction in certain individuals, and may even be the cause of phototoxic or photoallergic reactions. It is thus desirable also to screen out UV-A radiation.

Many cosmetic compositions intended for photoprotecting the skin (against UV-A and/or UV-B) have been proposed to date.

These antisun compositions are quite often in the form of an emulsion of oil-in-water type (i.e. a cosmetically acceptable support consisting of an aqueous dispersing continuous phase and an oily dispersed discontinuous phase) which contains, in various concentrations, one or more standard, lipophilic and/or hydrophilic organic screening agents capable of selectively absorbing harmful UV radiation, these screening agents (and the amounts thereof) being selected as a function of the desired protection factor (SPF), which is expressed mathematically by the ratio of the irradiation time required to reach the erythema-forming threshold with the UV screening agent to the time required to reach the erythema-forming threshold without a UV screening agent.

SUMMARY OF THE INVENTION

Now, after considerable research conducted in the photoprotection field mentioned above, the applicants have discovered, surprisingly and unexpectedly, that a combination of two specific sun screens which are already known per se in the state of the art gives, on account of a synergy effect, antisun compositions whose sun protection factors are markedly improved, and in any case better than those which can be obtained, for an equal concentration of screening agent and for a support of identical nature, with one or other of the screening agents used alone.

This discovery forms the basis of the present invention.

Thus, in accordance with one of the subjects of the present invention, novel cosmetic compositions, in particular antisun compositions, are now proposed which are essentially characterized in that they comprise, in a cosmetically acceptable support, (i) as first screening agent, a specific 1,3,5-triazine derivative which will be defined in greater detail later, and (ii) as second screening agent, a specific silicon derivative containing a specific benzotriazole function, which will be defined in greater detail later; the said first and second screening agents being present in the said compositions in an amount which is effective for producing synergistic activity in terms of the sun protection factors imparted.

A subject of the present invention is also the use of such compositions as, or for the manufacture of, cosmetic compositions intended for protecting the skin and/or the hair against ultraviolet radiation, in particular solar radiation.

Yet another subject of the present invention is a cosmetic treatment process for protecting the skin and/or the hair against ultraviolet radiation, in particular solar radiation, and which consists essentially in applying an effective amount of a composition in accordance with the invention to the skin and/or the hair.

Other characteristics, aspects and advantages of the present invention will become apparent on reading the detailed description which follows.

DETAILED DESCRIPTION OF BEST MODE AND SPECIFIC/PREFERRED EMBODIMENTS OF THE INVENTION

The 1,3,5-triazine derivatives in accordance with the invention correspond to the following general formula:

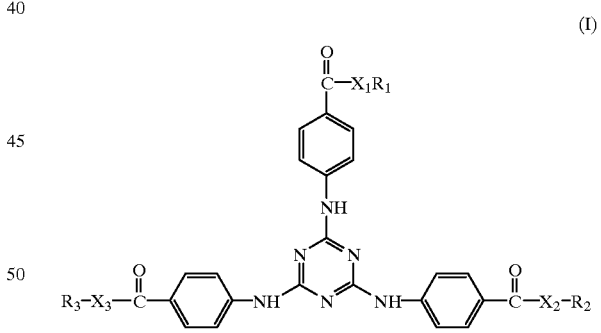

in which:
- $X_1$, $X_2$ and $X_3$, which may be identical or different, represent oxygen or a radical —NR—;
- the radicals R, which may be identical or different, denote hydrogen or a linear or branched $C_1$–$C_{18}$ alkyl radical or a $C_5$–$C_{12}$ cycloalkyl radical which may be substituted with one or more $C_1$–$C_4$ alkyl radicals;
- $R_1$, $R_2$ and $R_3$, which may be identical or different, are chosen from: hydrogen; an alkali metal; an ammonium radical optionally substituted with one or more alkyl or hydroxyalkyl radicals; a linear or branched $C_1$–$C_{18}$ alkyl radical; a $C_5$–$C_{12}$ cycloalkyl radical optionally substituted with one or more $C_1$–$C_4$ alkyl radicals; a polyoxyethylenated radical comprising from 1 to 6 ethylene oxide units and in which the end OH group is methylated; a radical of formula (II), (III) or (IV) below:

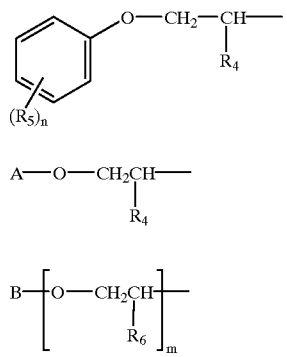

(II)

(III)

(IV)

in which:
R$_4$ is hydrogen or a methyl radical;
R$_5$ is a C$_1$–C$_9$ alkyl radical;
n is an integer ranging from 0 to 3;
m is an integer ranging from 1 to 10;
A is a C$_4$–C$_8$ alkyl radical or a C$_5$–C$_8$ cycloalkyl radical;
B is chosen from: a linear or branched C$_1$–C$_8$ alkyl radical; a C$_5$–C$_8$ cycloalkyl radical; an aryl radical optionally substituted with one or more C$_1$–C$_4$ alkyl radicals;
R$_6$ is hydrogen or a methyl radical.

A first preferred family of 1,3,5-triazine derivatives is the one described in particular in document EP-A-0,517,104 (the teachings of which are, as regards the actual definition of these products, entirely included in the present description by way of reference) for the 1,3,5-triazines corresponding to formula (I) above and having all of the following characteristics:

X$_1$, X$_2$ and X$_3$ are identical and represent oxygen;
R$_1$ is chosen from: a C$_5$–C$_{12}$ cycloalkyl radical optionally substituted with one or more C$_1$–C$_4$ alkyl radicals; a radical of formula (II), (III) or (IV) above in which:
B is a C$_1$–C$_4$ alkyl radical;
R$_6$ is a methyl radical;
R$_2$ and R$_3$, which may be identical or different, are chosen from: hydrogen; an alkali metal; an ammonium radical optionally substituted with one or more alkyl or hydroxyalkyl radicals; a linear or branched C$_1$–C$_{18}$ alkyl radical; a C$_5$–C$_{12}$ cycloalkyl radical optionally substituted with one or more C$_1$–C$_4$ alkyl radicals; a radical of formula (II), (III) or (IV) above in which:
B is a C$_1$–C$_4$ alkyl radical;
R$_6$ is a methyl radical.

A second preferred family of 1,3,5-triazine derivatives according to the invention is the one described in particular in document EP-A-0,570,838 (the teachings of which are, as regards the actual definition of these products, entirely included in the present description by way of reference) for the 1,3,5-triazines corresponding to formula (I) and having all of the following characteristics:

X$_1$ is oxygen; X$_2$ is an —NH— radical or oxygen;
X$_3$ is an —NH— radical;
R$_3$ is chosen from: a linear or branched C$_1$–C$_{18}$ alkyl radical; a C$_5$–C$_{12}$ cycloalkyl radical optionally substituted with one or more C$_1$–C$_4$ alkyl radicals;
R$_1$ is chosen from: hydrogen; an alkali metal; an ammonium radical; a radical of formula (IV); a linear or branched C$_1$–C$_{18}$ alkyl radical; a C$_5$–C$_{12}$ cycloalkyl radical optionally substituted with one or more C$_1$–C$_4$ alkyl radicals;
if X$_2$ is an —NH— radical, then R$_2$ is chosen from: a linear or branched C$_1$–C$_{18}$ alkyl radical; a C$_5$–C$_{12}$ cycloalkyl radical optionally substituted with one or more C$_1$–C$_4$ alkyl radicals;
if X$_2$ is oxygen, then R$_2$ is chosen from: hydrogen; an alkali metal; an ammonium radical; a radical of formula (IV); a linear or branched C$_1$–C$_{18}$ alkyl radical; a C$_5$–C$_{12}$ cycloalkyl radical optionally substituted with one or more C$_1$–C$_4$ alkyl radicals.

A third preferred family of 1,3,5-triazine derivatives according to the invention is the one described in particular in document EP-A-0,796,851 (the teachings of which are, as regards the actual definition of these products, entirely included in the present description by way of reference) for the 1,3,5-triazines corresponding to formula (I) and having all of the following characteristics:

X$_1$, X$_2$ and X$_3$ simultaneously denote —NR—;
the radicals R, which may be identical or different, denote hydrogen or a linear or branched C$_1$–C$_{18}$ alkyl radical or a C$_5$–C$_{12}$ cycloalkyl radical which may be substituted with one or more C$_1$–C$_4$ alkyl radicals;
R$_1$, R$_2$ and R$_3$, which may be identical or different, denote hydrogen or a radical R.

A preferred 1,3,5-triazine is 2,4,6-tris[p-(2'-ethylhexyl-1'-oxycarbonyl)anilino]-1,3,5-triazine which is a screening agent known per se, which is active in the UV-B range, which is in solid form and which is sold in particular under the trade name "Uvinul T150" by the company BASF. This product corresponds to the following formula:

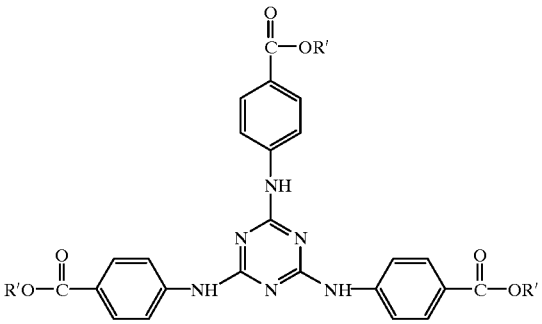

in which R' denotes a 2-ethylhexyl radical.

A 1,3,5-triazine according to the invention which is particularly preferred is the one corresponding to the following formula:

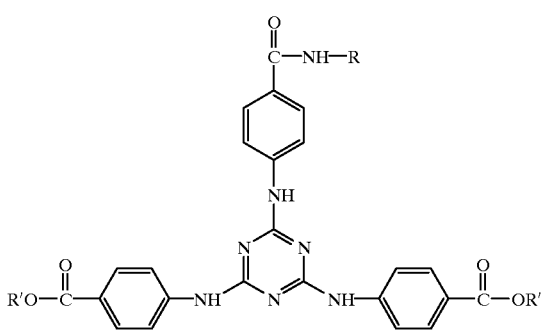

in which R' denotes a 2-ethylhexyl radical and R denotes a tert-butyl radical.

The triazine derivative(s) may be present in the compositions according to the invention in a content ranging from 0.1 to 20%, preferably from 0.2 to 15%, by weight, always relative to the total weight of the composition.

The silicon derivatives containing a benzotriazole function, which are used in the present invention, are silanes or siloxanes containing a benzotriazole function, comprising at least one unit of formula (1) below:

$$O_{(3-8)/2}Si(R_7)_a-G \qquad (1)$$

in which:
R$_7$ represents an optionally halogenated C$_1$–C$_{10}$ alkyl radical or a phenyl radical or a trimethylsilyloxy radical,
a is an integer chosen between 0 and 3 inclusive, and
the symbol G denotes a monovalent radical linked directly to a silicon atom, and which corresponds to formula (2) below:

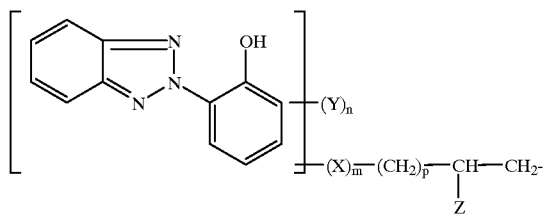

which:
Y, which may be identical or different, are chosen from C$_1$–C$_8$ alkyl radicals, halogens and C$_1$–C$_4$ alkoxy radicals, it being understood that, in the latter case, two adjacent groups Y on the same aromatic ring can together form an alkylidenedioxy group in which the alkylidene group contains 1 or 2 carbon atoms,
X represents O or NH,
Z represents hydrogen or a C$_1$–C$_4$ alkyl radical,
n is an integer between 0 and 3 inclusive,
m is 0 or 1,
p represents an integer between 1 and 10 inclusive.

These compounds are described in particular in patent application EP-A-711,778 assigned to the assignee hereof, as well as in patent application WO 94/06404, also assigned to the assignee hereof.

Preferably, the silicon derivatives used in the context of the present invention belong to the general family of benzotriazole silicones which is described in particular in WO 94/06404.

One family of benzotriazole silicones which is particularly suitable for carrying out the present invention is the one which combines the compounds corresponding to formula (5) or (6) below:

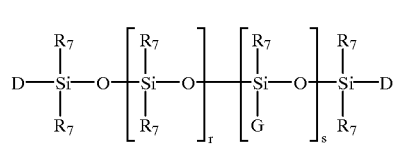

or

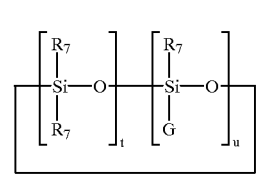

in which:
R$_7$, which may be identical or different, are chosen from C$_1$–C$_{10}$ alkyl, phenyl, 3,3,3-trifluoropropyl and trimethylsilyloxy radicals, at least 80%, in numerical terms, of the radicals R$_7$ being methyl,
D, which may be identical or different, are chosen from the radicals R$_7$ and the radical G,
r is an integer between 0 and 50 inclusive, and s is an integer between 0 and 20 inclusive, and if s=0, at least one of the two symbols D denotes G,
u is an integer between 1 and 6 inclusive, and t is an integer between 0 and 10 inclusive, it being understood that t+u is equal to or greater than 3, and
the symbol G corresponds to formula (2) above.

As emerges from formula (2) given above, attachment of the chain unit —(X)$_m$—(CH$_2$)$_p$—CH(Z)—CH$_2$— to the benzotriazole unit, which thus ensures connection of the said benzotriazole unit to the silicon atom in the silicone chain, can, according to the present invention, take place in any of the available positions offered by the two aromatic rings of the benzotriazole:

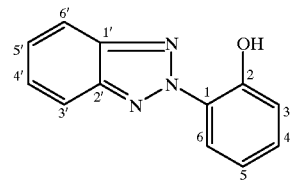

Preferably, this attachment takes place in position 3, 4, 5 (aromatic ring bearing the hydroxyl function) or 4' (benzene ring adjacent to the triazole ring), and even more preferably in position 3, 4 or 5. In a preferred embodiment of the invention, the attachment takes place in position 3.

Similarly, the attachment of the substituent unit(s) Y can take place in any of the other available positions on the benzotriazole. However, preferably, this attachment takes place in position 3, 4, 4', 5 and/or 6. In a preferred embodiment of the invention, attachment of the unit Y takes place in position 5.

In formulae (5) and (6) above, the alkyl radicals can be linear or branched and chosen in particular from methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred alkyl radicals $R_7$ according to the invention are methyl, ethyl, propyl, n-butyl, n-octyl and 2-ethylhexyl radicals. Even more preferably, the radicals $R_7$ are all methyl radicals.

Among the compounds of formula (5) or (6) above, it is preferred to use those corresponding to the formula (5), i.e. diorganosiloxanes containing a short linear chain.

Among the compounds of formula (5) above, it is preferred to use those for which the radicals D are both radicals $R_7$.

Among the linear diorganosiloxanes falling within the context of the present invention, the ones more particularly preferred are random derivatives or derivatives in well-defined blocks, which have at least one, and even more preferably all, of the following characteristics:

D is a radical $R_7$, $R_7$ is alkyl and even more preferably is methyl, r is between 0 and 15 inclusive; s is between 1 and 10 inclusive, n is non-zero and preferably equal to 1, and Y is then chosen from methyl, tert-butyl or $C_1$–$C_4$ alkoxy, Z is hydrogen or methyl, m=0, or [m=1 and X=O]

p is equal to 1.

One family of benzotriazole silicones which is particularly suitable for the invention is the one defined by the general formula (7) below:

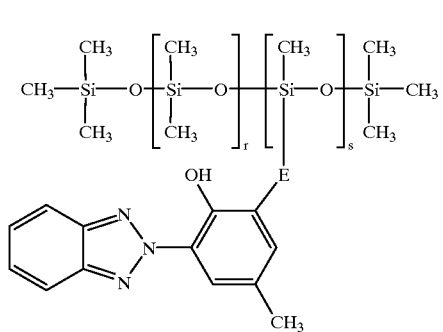

(7)

with $0 \leq r \leq 10$, $1 \leq s \leq 10$, and in which E represents the divalent radical:

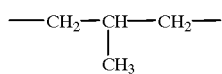

In a particularly preferred embodiment of the invention, the benzotriazole silicone is the compound (referred to in the text hereinbelow as compound (a)) corresponding to the following formula:

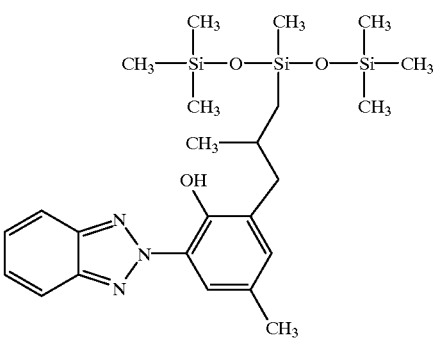

compound (a)

Processes which are suitable for preparing the products of formula (1), (5), (6) and (7) above are described in particular in U.S. Pat. Nos. 3,220,972, 3,697,473, 4,340,709, 4,316,033 and 4,328,346 and in patent applications EP-A-0,392,883 and EP-A-0,742,003.

The silicon derivative containing a benzotriazole function can be present in the compositions according to the invention in contents ranging from 0.1 to 20%, preferably ranging from 0.2 to 15%, by weight, always relative to the total weight of the composition.

In practical terms, the above two screening agents, i.e. the triazine derivative and the silicon derivative containing a benzotriazole unit, are, needless to say, preferably both present in the final composition in respective proportions chosen such that the synergistic effect, on the sun protection factor imparted by the resulting combination, is optimal.

According to a preferred embodiment of the present invention, the compositions according to the invention are emulsions of oil-in-water type.

The antisun cosmetic compositions according to the invention can, needless to say, contain one or more additional hydrophilic or lipophilic sun screens which are active in the UVA and/or UVB range (absorbers) other than, of course, the two screening agents mentioned above. These additional screening agents can be chosen in particular from cinnamic derivatives, salicylic derivatives, camphor derivatives, benzophenone derivatives, dibenzoylmethane derivatives, β,β-diphenylacrylate derivatives, p-aminobenzoic acid derivatives, screening polymers and screening silicones other than those containing a benzotriazole function, in particular those described in patent application WO 93/04665. Other examples of organic screening agents are given in patent application EP-A-487,404.

The compositions according to the invention can also contain agents for artificially tanning and/or browning the skin (self-tanning agents) such as, for example, dihydroxyacetone (DHA).

The cosmetic compositions according to the invention can also contain pigments or nanopigments (average primary particle size: generally between 5 nm and 100 nm, preferably between 10 nm and 50 nm) of coated or uncoated metal oxides such as, for example, nanopigments of titanium oxide (amorphous or crystallized in rutile and/or anatase form), of iron oxide, of zinc oxide, of zirconium oxide or of cerium oxide, which are all UV photoprotective agents that are well known per se. Other standard coating agents are alumina and/or aluminium stearate. Such coated or uncoated metal oxide nanopigments are described in particular in patent applications EP-A-0,518,772 and EP-A-0,518,773.

The compositions of the invention can also comprise standard cosmetic adjuvants chosen in particular from fatty substances, organic solvents, ionic or nonionic thickeners, softeners, antioxidants, opacifiers, stabilizers, emollients, silicones, α-hydroxy acids, antifoaming agents, moisturizers, vitamins, fragrances, preserving agents, surfactants, fillers, sequestering agents, polymers, propellants, basifying or acidifying agents, dyes or any other ingredients usually used in cosmetics, in particular for manufacturing antisun compositions in the form of emulsions.

The fatty substances can consist of an oil or a wax or mixtures thereof, and they also comprise fatty acids, fatty alcohols and fatty acid esters. The oils can be chosen from animal, plant, mineral or synthetic oils and in particular from liquid petroleum jelly, liquid paraffin, volatile or non-volatile silicone oils, isoparaffins, poly-α-olefins, fluoro oils and perfluoro oils. Similarly, the waxes can be chosen from animal, fossil, plant, mineral or synthetic waxes which are known per se.

Among the organic solvents, mention may be made of lower alcohols and polyols.

The thickeners can be chosen in particular from crosslinked polyacrylic acids, modified or non-modified guar gums and cellulose gums, such as hydroxypropyl guar gum, methylhydroxylethylcellulose, hydroxypropylmethylcellulose or hydroxyethylcellulose.

Needless to say, a person skilled in the art will take care to select this or these optional additional compounds and/or the amounts thereof such that the advantageous properties, in particular the synergistic effect, intrinsically associated with the binary combination in accordance with the invention are not, or are not substantially, adversely affected by the addition(s) envisaged.

The compositions of the invention can be prepared according to the techniques which are well known to those skilled in the art, in particular those techniques intended for the preparation of oil-in-water or water-in-oil type emulsions.

This composition can be, in particular, in the form of a simple or complex (O/W, W/O, O/W/O or W/O/W) emulsion such as a cream, a milk, a gel or a cream-gel, or in the form of a powder or a solid tube, and can optionally be packaged as an aerosol and be in the form of a mousse or a spray.

When the composition is an emulsion, the aqueous phase of this emulsion can comprise a nonionic vesicle dispersion prepared according to known processes (Bangham, Standish and Watkins, J. Mol. Biol. 13, 238 (1965), FR 2,315,991 and FR 2,416,008).

The cosmetic composition of the invention can be used as a composition for protecting the human epidermis or the hair against ultraviolet rays, as an antisun composition or as a make-up product.

The cosmetic composition of the invention can also be used as a composition for protecting the natural colour of or artificial tints on the hair against the harmful effects of ultraviolet rays.

When the cosmetic composition according to the invention is used for protecting the human epidermis against UV rays, or as an antisun composition, it can be in the form of a suspension or a dispersion in solvents or fatty substances, in the form of a nonionic vesicle dispersion or else in the form of an emulsion, preferably of oil-in-water type, such as a cream or a milk, in the form of an ointment, a gel, a cream-gel, a solid tube, a stick, an aerosol mousse or a spray.

When the cosmetic composition according to the invention is used for protecting the hair, it can be in the form of a shampoo, a lotion, a gel, an emulsion, a nonionic vesicle dispersion or a lacquer for the hair and can constitute, for example, a rinse-out composition, to be applied before or after shampooing, before or after dyeing or bleaching, before, during or after permanent-waving or straightening the hair, a styling or treating lotion or gel, a blow-drying or hair setting lotion or gel or a composition for permanently reshaping, straightening, dyeing or bleaching the hair.

When the composition is used as a make-up product for the eyelashes, the eyebrows or the skin, such as an epidermal treatment cream, a foundation, a tube of lipstick, an eyeshadow, a blusher, a mascara or an eyeliner, it can be in solid or pasty, anhydrous or aqueous form, such as oil-in-water or water-in-oil emulsions, nonionic vesicle dispersions or suspensions.

As a guide, for the antisun formulations in accordance with the invention which contain a support of oil-in-water emulsion type, the aqueous phase (in particular comprising the hydrophilic screening agents) generally represents from 50 to 95% by weight, preferably from 70 to 90% by weight, relative to the whole formulation, the oily phase (in particular comprising the lipophilic screening agents) generally represents from 5 to 50% by weight, preferably from 10 to 30% by weight, relative to the whole formulation, and the (co)emulsifier(s) generally represent(s) from 0.5 to 20% by weight, preferably from 2 to 10% by weight, relative to the whole formulation.

Another subject of the present invention is a cosmetic treatment process for the skin or the hair which is intended to protect them against the effects of UV rays, this process consisting in applying an effective amount of a cosmetic composition as defined above to the skin or the hair.

Another subject of the present invention is a cosmetic treatment process for the hair which is intended to protect its natural colour or its artificial coloration against the effects of UV rays, this process consisting in applying an effective amount of a cosmetic composition as defined above to the hair.

Lastly, another subject of the invention consists in using a composition containing the specific combination of UV screening agents as defined above, as a photoprotective agent in, and for the manufacture of, cosmetic or dermopharmaceutical compositions.

Concrete, but in no way limiting, examples illustrating the invention will now be given.

EXAMPLES

| Composition | (A) | (B) | (C) |
|---|---|---|---|
| 80/20 mixture of cetylstearyl alcohol/oxyethylenated (33 EO) cetylstearyl alcohol ("Empiwax CL" Albright & Wilson) | 7 | 7 | 7 |
| Mixture of glyceryl mono- and distearate ("Cerasynth SD" ISP) | 2 | 2 | 2 |
| Cetyl alcohol | 1.5 | 1.5 | 1.5 |
| Polydimethylsiloxane ("DC200 fluid" Dow Corning) | 1.5 | 1.5 | 1.5 |
| $C_{12}/C_{15}$ alkyl benzoate ("Finsolv TN" Finetex) | 25 | 25 | 25 |
| Glycerol | 20 | 20 | 20 |
| Preserving agents | qs | qs | qs |
| (*) Triazine derivative of formula (I) | 5 | — | 3 |
| (**) Silicone containing a benzotriazole function, of formula (7) | — | 5 | 2 |
| Demineralized water qs | 100 g | 100 g | 100 g |

(*) The triazine derivative of formula (I) used has the structure:

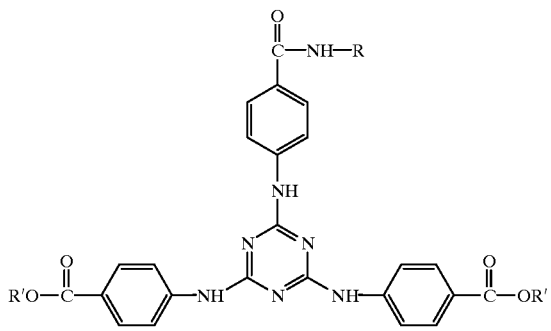

in which R' denotes a 2-ethylhexyl radical and R denotes a tert-butyl radical.

(**) The silicone containing a benzotriazole function has the structure:

compound (a)

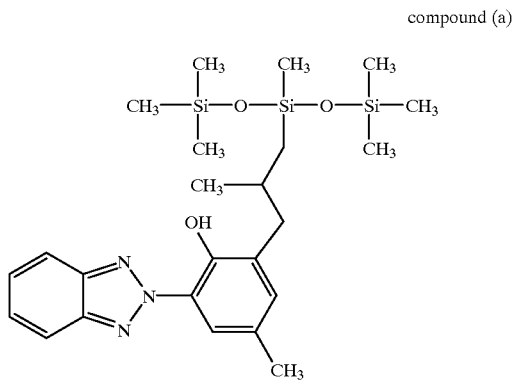

For each of these formulations (A), (B) and (C), the sun protection factor (SPF) associated therewith was then determined. This was determined using the in vitro method described by B. L. Diffey et al. in J. Soc. Cosmet. Chem. 40-127-133 (1989); this method consists in determining the monochromatic protection factors every 5 nm over a wavelength range from 290 to 400 nm and, using these factors, in calculating the sun protection factor according to a given mathematical equation.

The compositions of the various formulations studied and the results in terms of average sun protection factor (average of three tests) obtained are collated in Table (I) given below.

TABLE (I)

| Composition | "in vitro" SPF | Standard deviation |
|---|---|---|
| (A) (outside the invention) | 6.8 | 0.6 |
| (B) (outside the invention) | 5.2 | 1.0 |
| (C) (invention) | 9.7 | 0.8 |

These results show the synergy of the combination—triazine derivative/silicone containing a benzotriazole function—in terms of efficacy of the sun protection.

What is claimed is:

1. A topically applicable cosmetic/dermatological sunscreen composition suited for the UV-photoprotection of human skin and/or hair, comprising UV-photoprotecting SPF-synergistically effective amounts of (i) at least one 1,3,5-triazine UV-screening compound having the structural formula

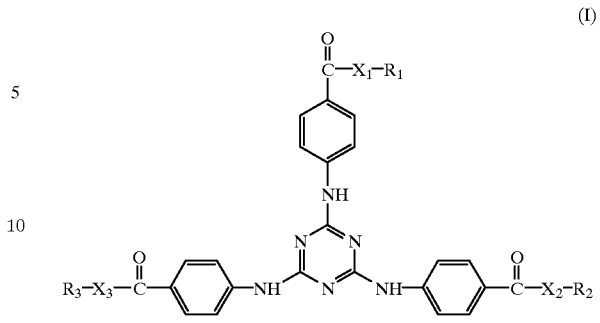

in which $X_1$, $X_2$, $X_3$, which may be identical or different, are each an oxygen atom or a radical —NR—, wherein the radicals R, which may be identical or different, are each a hydrogen atom, or a linear or branched $C_1$–$C_{18}$ alkyl radical, or a $C_5$–$C_{12}$ cycloalkyl radical optionally substituted with one or more $C_1$–$C_4$ alkyl radicals; $R_1$, $R_2$ and $R_3$, which may be identical or different, are each a hydrogen atom, an alkali metal, an ammonium radical optionally substituted with one or more alkyl or hydroalkyl radicals, a linear or branched $C_1$–$C_{18}$ alkyl radical, a $C_5$–$C_{12}$ cycloalkyl radical optionally substituted with one or more $C_1$–$C_4$ alkyl radicals, a polyoxyethylenated radical comprising from 1 to 6 ethylene oxide units and in which the OH endgroup is methylated, or a radical having one of the formulae (II), (III) or (IV) below:

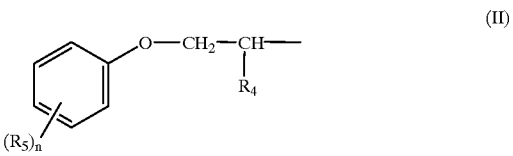

in which $R_4$ is a hydrogen atom or a methyl radical; $R_5$ is a $C_1$–$C_9$ alkyl radical; n is an integer ranging from 0 to 3; m is an integer ranging from 1 to 10; A is a $C_4$–$C_8$ alkyl radical or a $C_5$–$C_8$ cycloalkyl radical; B is a linear or branched $C_1$–$C_8$ alkyl radical, a $C_5$–$C_8$ cycloalkyl radical, an aryl radical optionally substituted with one or more $C_1$–$C_4$ alkyl radicals; and $R_6$ is a hydrogen atom or a methyl radical; and (ii) at least one benzotriazole-substituted silicon UV-screening compound which comprises at least one structural unit having the formula (1):

in which $R_7$ is an optionally halogenated $C_1$–$C_{10}$ alkyl radical, or a phenyl radical, or a trimethylsilyloxy radical; a is an integer ranging from 0 to 3, inclusive; and G is a monovalent radical directly bonded to a silicon atom, and which has the formula (2):

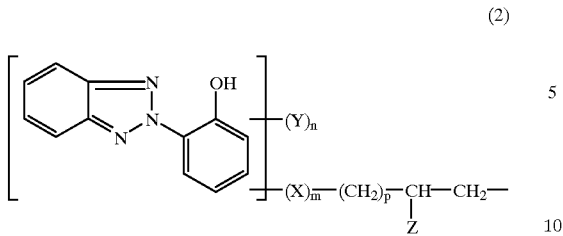

(2)

in which the radicals Y, which may be identical or different, are each a $C_1$–$C_8$ alkyl radical, a halogen atom, or a $C_1$–$C_4$ alkoxy radical, with the proviso that, in the latter case, two adjacent radicals Y on the same aromatic ring member can together form an alkylidenedioxy group in which the alkylidene moiety has 1 or 2 carbon atoms; X is O or NH; Z is a hydrogen atom or a $C_1$–$C_4$ alkyl radical; n is an integer ranging from 0 to 3, inclusive; m is 0 or 1; and p is an integer ranging from 1 to 10, inclusive; formulated into a topically applicable, cosmetically/dermatologically acceptable support therefor.

2. The cosmetic/dermatological sunscreen composition as defined by claim 1, wherein formula (I), $X_1$, $X_2$ and $X_3$ are identical and each is an oxygen atom; $R_1$ is a $C_5$–$C_{12}$ cycloalkyl radical optionally substituted with one or more $C_1$–$C_4$ alkyl radicals, or a radical of formula (II), (III) or (IV) in which B is a $C_1$–$C_4$ alkyl radical, and $R_6$ is a methyl radical; $R_2$ and $R_3$, which may be identical or different, are each a hydrogen atom, an alkali metal, an ammonium radical optionally substituted with one or more alkyl or hydroxyalkyl radicals, a linear or branched $C_1$–$C_{18}$ alkyl radical, a $C_5$–$C_{12}$ cycloalkyl radical optionally substituted with one or more $C_1$–$C_4$ alkyl radicals, or a radical of formula (II), (III) or (IV) in which B is a $C_1$–$C_4$ alkyl radical, and $R_6$ is a methyl radical.

3. The cosmetic/dermatological sunscreen composition as defined by claim 1, wherein formula (I), $X_1$ is an oxygen atom; $X_2$ is an —NH— radical or an oxygen atom; $X_3$ is an —NH— radical; $R_3$ is a linear or branched $C_1$–$C_{18}$ alkyl radical, or a $C_5$–$C_{12}$ cycloalkyl radical optionally substituted with one or more $C_1$–$C_4$ alkyl radicals; $R_1$ is a hydrogen atom, an alkali metal, an ammonium radical, a radical of formula (IV), a linear or branched $C_1$–$C_{18}$ alkyl radical, or a $C_5$–$C_{12}$ cycloalkyl radical optionally substituted with one or more $C_1$–$C_4$ alkyl radicals; with the proviso that, if $X_2$ is an —NH— radical, then $R_2$ is a linear or branched $C_1$–$C_{18}$ alkyl radical, or a $C_5$–$C_{12}$ cycloalkyl radical optionally substituted with one or more $C_1$–$C_4$ alkyl radicals; and with the further proviso that, if $X_2$ is an oxygen atom, then $R_2$ is hydrogen atom, an alkali metal, an ammonium radical, a radical of formula (IV), a linear or branched $C_1$–$C_{18}$ alkyl radical, or a $C_5$–$C_{12}$ cycloalkyl radical optionally substituted with one or more $C_1$–$C_4$ alkyl radicals.

4. The cosmetic/dermatological sunscreen composition as defined by claim 1 wherein formula (I), $X_1$, $X_2$ and $X_3$ are each an —NR— radical; the radicals R, which may be identical or different, are each a hydrogen atom, or a linear or branched $C_1$–$C_{18}$ alkyl radical, or a $C_5$–$C_{12}$ cycloalkyl radical optionally substituted with one or more $C_1$–$C_4$ alkyl radicals; and $R_1$, $R_2$ and $R_3$, which may be identical or different, are each a hydrogen atom or a radical R.

5. The cosmetic/dermatological sunscreen composition as defined by claim 1, said at least one 1,3,5-triazine UV-screening compound (I) having the formula:

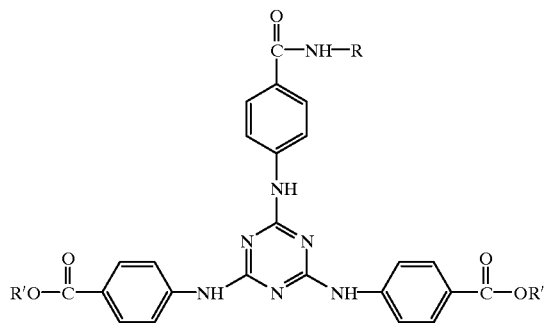

in which R' is a 2-ethylhexyl radical and R is a tert-butyl radical.

6. The cosmetic/dermatological sunscreen composition as defined by claim 1, said at least one 1,3,5-triazine UV-screening compound (I) having the formula:

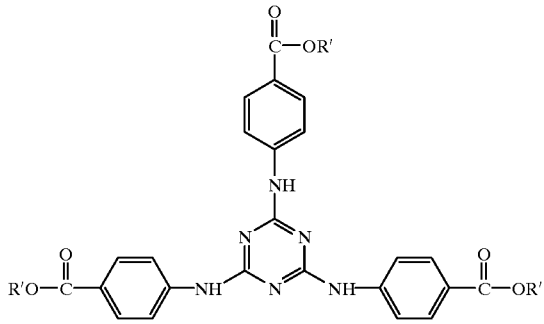

in which R' is a 2-ethylhexyl radical.

7. The cosmetic/dermatological sunscreen composition as defined by claim 1, comprising from 0.5% to 20% by weight of said at least one 1,3,5-triazine UV-screening compound (i).

8. The cosmetic/dermatological sunscreen composition as defined by claim 7, comprising from 1% to 10% by weight of said at least one 1,3,5-triazine UV-screening compound (i).

9. The cosmetic/dermatological sunscreen composition as defined by claim 1, said at least one benzotriazole-substituted silicon UV-screening compound (ii) having one of the structural formulae (5) or (6):

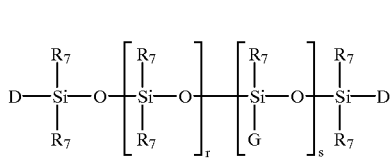

(5)

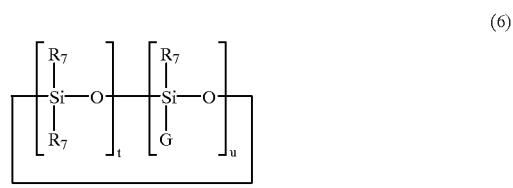

(6)

in which the radicals $R_7$, which may be identical or different, are each a $C_1$–$C_{10}$ alkyl, phenyl, 3,3,3-trifluoropropyl or trimethylsilyloxy radical, at least 80%, in numerical terms, of the radicals $R_7$ being methyl radicals; the radicals D, which may be identical or different, are each a radical $R_7$ or a radical G; r is an integer ranging from 0 to 50, inclusive, and s is an integer ranging from 0 to 20, inclusive, with the proviso that, if s=0, at least one of the two radicals D is a radical G; u is an integer ranging from 1 to 6, inclusive, and t is an integer ranging from 0 to 10, inclusive, with the proviso that t+u is equal to or greater than 3; and G is a monovalent radical directly bonded to a silicon atom and having the formula (2).

10. The cosmetic/dermatological sunscreen composition as defined by claim 9, said at least one benzotriazole-substituted silicon UV-screening compound (ii) having the structural formula (5).

11. The cosmetic/dermatological sunscreen composition as defined by claim 9, said at least one benzotriazole-substituted silicon UV-screening compound (ii) having the structural formula (6).

12. The cosmetic/dermatological sunscreen composition as defined by claim 9, said at least one benzotriazole-substituted silicon UV-screening compound (ii) having the structural formula (7):

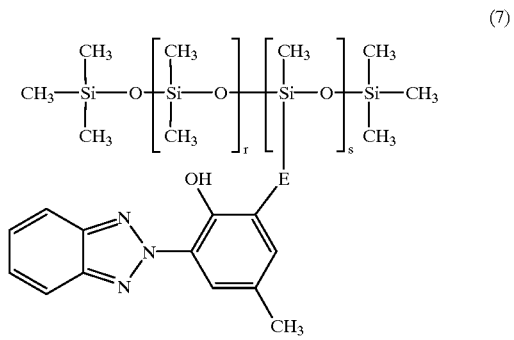

(7)

in which $0 \leq r \leq 10$; $1 \leq s \leq 10$; and E is the divalent radical:

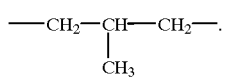

13. The cosmetic/dermatological sunscreen composition as defined by claim 12, said at least one benzotriazole-substituted silicon UV-screening compound (ii) having the structural formula:

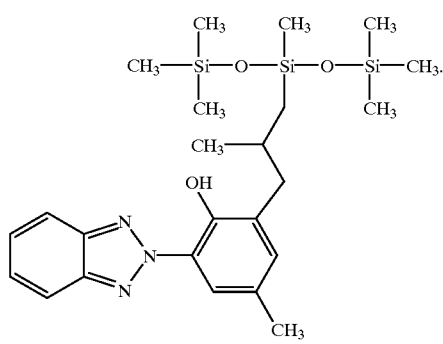

14. The cosmetic/dermatological sunscreen composition as defined by claim 9, comprising from 0.1% to 20% by weight of said at least one benzotriazole-substituted silicon UV-screening compound (ii).

15. The cosmetic/dermatological sunscreen composition as defined by claim 14, comprising from 0.2% to 15% by weight of said at least one benzotriazole-substituted silicon UV-screening compound (ii).

16. The cosmetic/dermatological sunscreen composition as defined by claim 1, formulated as an emulsion, cream, gel, milk, cream-gel, powder, solid, stick, suspension, mousse, spray, or vesicle dispersion.

17. The cosmetic/dermatological sunscreen composition as defined by claim 16, formulated as an oil-in-water emulsion.

18. The cosmetic/dermatological sunscreen composition as defined by claim 16, comprising a make-up product.

19. The cosmetic/dermatological sunscreen make-up product as defined by claim 18, comprising an epidermal treatment cream, a foundation, a lipstick, an eyeshadow, a blusher, a mascara, or an eyeliner.

20. The cosmetic/dermatological sunscreen composition as defined by claim 16, comprising a shampoo, a hair lacquer, a rinse, a hair styling/treating lotion or gel, or a hair reshaping, straightening, dyeing or bleaching formulation.

21. The cosmetic/dermatological sunscreen composition as defined by claim 1, further comprising at least one other UV-A and/or UV-B screening agent.

22. The cosmetic/dermatological sunscreen composition as defined by claim 1, further comprising at least one active agent for the artificial tanning and/or browning of human skin.

23. The cosmetic/dermatological sunscreen composition as defined by claim 1, further comprising a photoprotecting effective amount of particulates of at least one inorganic pigment or nanopigment.

24. The cosmetic/dermatological sunscreen composition as defined by claim 1, further comprising at least one cosmetically/dermatologically acceptable additive or adjuvant.

25. The cosmetic/dermatological sunscreen compositoin as define by claim 24, said at least one adjuvant or additive comprising a fat, organic solvent, ionic or nonionic thickening agent, softener, antioxidant, opacifying agent, stabilizing agent, silicone, α-hydroxy acid, anti-foaming agent, hydrating agent, vitamin, fragrance, perservative, surfactant, filler, sequestering agent, emollient, moisturizer, polymer, propellant, insect repellent, basifying or acidifying agent, dye, or mixture thereof.

26. a regime/regimen for protecting human skin and/or hair against the damaging effects of UV-irradiation, comprising topically applying thereon an effective UV-photoprotecting amount of the cosmetic/dermatological sunscreen composition as defined by claim 1.

27. A regime/regimen for protecting human skin and/or hair against the damaging effects of solar irradiation, comprising topically applying thereon an effective solar radiation-photoprotecting amount of the cosmetic/dermatological sunscreen composition as defined by claim 1.

28. A regime/regimen for protecting the natural or artificial color of human hair against the damaging effects of UV-irradiation, comprising topically applying thereon an effective UV-photoprotecting, hair color-maintaining amount of the cosmetic/dermatological sunscreen composition as defined by claim 1.

* * * * *